United States Patent [19]
Iwahara

[11] Patent Number: 6,140,533
[45] Date of Patent: Oct. 31, 2000

[54] PROCESS FOR PRODUCING SEC-BUTYL ACRYLATE

[75] Inventor: Masahiro Iwahara, Tokuyama, Japan

[73] Assignee: Idemitsu Petrochemical Co., Ltd., Tokyo, Japan

[21] Appl. No.: 09/077,750

[22] PCT Filed: Dec. 6, 1996

[86] PCT No.: PCT/JP96/03583

§ 371 Date: Jul. 11, 1998

§ 102(e) Date: Jul. 11, 1998

[87] PCT Pub. No.: WO97/23444

PCT Pub. Date: Jul. 3, 1997

[30] Foreign Application Priority Data

Dec. 22, 1995 [JP] Japan .................................. 7-335398

[51] Int. Cl.$^7$ .................................................. C07C 69/52
[52] U.S. Cl. .......................................................... 560/205
[58] Field of Search ............................................... 560/205

[56] References Cited

U.S. PATENT DOCUMENTS 5,138,092 8/1992 Perez Pascual et al. ............... 560/205
5,596,126 1/1997 Riondel .................................... 560/205

*Primary Examiner*—Paul J. Killos
*Assistant Examiner*—Everett White
*Attorney, Agent, or Firm*—Antonelli, Terry, Stout & Kraus, LLP

[57] ABSTRACT

A process for producing sec-butyl acrylate which comprises reacting acrylic acid with at least one member selected among butene-1, trans-2-butene, and cis-2-butene in a liquid phase in the presence of an ion exchange resin containing sulfo groups while regulating the content of water in the reaction system to 0.01 to 1.50 wt % based on the whole system, the reaction temperature to 40 to 120° C., and the molar ratio of butene/acrylic acid to 1 to 6. According to this process, sec-butyl acrylate can be produced with a high selectivity and a high conversion while inhibiting catalyst deterioration.

15 Claims, No Drawings

PROCESS FOR PRODUCING SEC-BUTYL ACRYLATE

TECHNICAL FIELD

The present invention relates to a process for producing sec-butyl acrylate with a high selectivity and a high conversion ratio, while inhibiting catalyst deterioration.

BACKGROUND ART

Japanese Patent Application Examined Publication No. 6-104645 discloses a process for producing sec-butyl acrylate by allowing acrylic acid to react with 1-butene in the presence of ion exchange resins having sulfo groups. Although this process is excellent in selectivity and conversion ratio, there is a demand for processes for producing sec-butyl acrylate further excelling in selectivity and conversion ratio.

DISCLOSURE OF INVENTION

The object of the present invention is to improve the above-described process, thereby providing a process for producing sec-butyl acrylate with a higher selectivity and a higher conversion ratio, while inhibiting catalyst deterioration.

As the results of researches for achieving the object, the inventor has found that a high selectivity toward sec-butyl acrylate, a high conversion ratio and the inhibition of catalyst deterioration can be attained by carrying out the reaction of acrylic acid with specific butenes in the presence of ion exchange resins having sulfo groups in a liquid phase reaction system containing 0.01 to 1.50 wt % of water, and has completed the present invention based on the finding.

That is, the present invention provides a process for producing sec-butyl acrylate, comprising allowing acrylic acid to react with a butene selected from the group consisting of butene-1, trans-2-butene and cis-2-butene, in a molar ratio of butene/acrylic acid ranging from 1 to 6, in the presence of an ion exchange resin having sulfo groups, in a liquid-phase reaction system containing 0.01 to 1.50 wt % of water, at a reaction temperature of 40 to 120° C.

BEST MODE FOR CARRYING OUT THE INVENTION

The butene to be used in the present invention is selected from the group consisting of butene-1, trans-2-butene and cis-2-butene, which may be used individually or as a mixture of two or three.

The molar ratio of butene to acrylic acid (butene/acrylic acid) ranges from 1 to 6, preferably from 2 to 5, more preferably from 3 to 4.

The ion exchange resin having sulfo groups to be used in the present invention may be selected from any ion exchange resins having sulfo groups. None-limitative examples of the ion exchange resins are those prepared by introducing sulfo groups into polymer substrates, for example, copolymers of polymerization monomers, such as styrene, with di- or more-functional crosslinking agents, such as divinylbenzene. It is possible to use commercial ion exchange resins, for example, AMBERLYST 15, AMBERLYST 16 (trade names, produced by Rohm & Haas Co., Ltd.), K2441, K2461, K2661 (trade names, produced by Bayer Aktiengesellschaft), DOWEX 88 and DOWEX MSC-1 (trade names, produced by The Dow Chemical Company).

These ion exchange resins are porous, and the preferred ion exchange resins have a BET surface area of 20 to 100 $m^2/g$, a maximum pore diameter of 1000 Å, a porosity of 20 to 80% and an ion exchange capacity of 0.5 to 3 milliequivalent/litter.

The amount of the ion exchange resins having sulfo groups is generally 2 to 20 wt %, preferably 4 to 15 wt %, based on acrylic acid.

The reaction is carried out in a liquid phase and may be performed by using a fixed bed or an agitation chamber, and also may be performed by a patch process or a continuous process.

The reaction of the process of the present invention should be carried out in the presence of 0.01 to 1.50 wt % of water in the reaction system. Herein, the terms "reaction system" mean a system comprising the reaction mixture of acrylic acid and butene, water and optional polymerization inhibitors, and the amount of the ion exchange resins used as catalysts is not included in the amount of the reaction system. If the water content in the reaction system is less than 0.01 wt % or more than 1.50 wt %, the selectivity and the conversion ratio toward sec-butyl acrylate will be decreased, and significant inhibition of catalyst deterioration cannot be expected. While industrial acrylic acid, industrial butenes and industrial ion exchange resins will give a reaction system containing about 0.008 wt % of water, according to the present invention, water is added to the reaction system so that the water content in the reaction system is adjusted to 0.01 to 1.50 wt %, preferably 0.01 to 1.00 wt %, more preferably 0.01 to 0.50 wt %. Previous to their use for the reaction, the ion exchange resins are preferably dehydrated to reduce the water content thereof to 0.001 wt % or less. The water contents in acrylic acid and in butenes may be measured with a Karl Fischer measuring instrument, and the water content in the ion exchange resins with a thermobalance.

The reaction is carried out at a reaction temperature of 40 to 120° C., preferably 50 to 120° C., more preferably 70 to 90° C., and preferably at a reaction pressure of 3.0 to 40 $kg/cm^2G$, more preferably 5.0 to 15 $kg/cm^2G$. If the reaction temperature and reaction pressure are beyond the above-described ranges, it may sometimes be impossible to attain a high selectivity and a high conversion ratio. Reaction time is generally 1 to 10 hours.

When the reaction is carried out by a continuous process, it is also desirable to carry out the reaction at a reaction temperature of 40 to 120° C., preferably 50 to 120° C., more preferably 70 to 90° C., at a reaction pressure of 3.0 to 40 $kg/cm^2G$, more preferably 5.0 to 15 $kg/cm^2G$. If the reaction temperature and reaction pressure are beyond the above-described range, it may sometimes be impossible to attain a high selectivity and a high conversion ratio. The continuous process is desirable carried out under the conditions such that the contact time (SV) of acrylic acid with the ion exchange resin used as a catalyst, namely [acrylic acid volumetric flow rate (cc/hr)]/[the amount of packed dry ion exchange resin (cc)] is 0.01 to 10 $hr^{-1}$.

Polymerization inhibitors for acrylic acid and acrylic esters are preferably added to the reaction system of the present invention in a concentration of 10 to 2,000 wt ppm based on acrylic acid. Non-limitative examples of the polymerization inhibitors are hydroquinone, phenothiazine, oxygen and hydroquinone monomethyl ether. The polymerization inhibitors effectively inhibit the polymerization of acrylic acid and the product acrylic esters.

The present invention will be described in more detail with reference to the following Examples. These Examples, however, are not to be construed to limit the scope of the invention.

EXAMPLES 1 TO 6 AND COMPARATIVE EXAMPLES 1 TO 3

In a 100 ml autoclave were charged 1.1 g of the catalyst as listed in Table 1, 16.0 g (0.222 mol) of acrylic acid and 0.016 g of hydroquinone (polymerization inhibitor), and 37.4 g (0.66 mol) of the liquid butene as listed in Table 1 was added thereto. Water was further added so that the reaction system contained water in the amount as listed in Table 1, and heating was then started. Reaction was carried out for three hours at the temperature as listed in Table 1. The reaction pressure was adjusted within a range of 10.5 to 5.5 kg/cm²G.

After the completion of the reaction, unreacted butene was removed, and the reaction liquid was analyzed by gas chromatography to obtain the conversion ratio of acrylic acid, the selectivity toward sec-butyl acrylate and the yield. The selectivity and the conversion ratio are listed in Table 2, and the Yield in Table 1.

TABLE 1

| | Catalyst | Water Content (wt %) | Reaction Temp. (° C.) | Butene | Yield of sec-butyl acrylate (%) |
|---|---|---|---|---|---|
| Example 1 | K2441 | 0.02 | 90 | 1-butene | 95.1 |
| Example 2 | AMBERLYST 15 | 0.05 | 90 | trans-2-butene | 94.0 |
| Example 3 | AMBERLYST 16 | 0.20 | 90 | 1-butene | 91.8 |
| Example 4 | DOWEX 88 | 0.05 | 80 | cis-2-butene | 95.8 |
| Example 5 | K2661 | 0.40 | 85 | 1-butene | 90.2 |
| Example 6 | K2661 | 1.2 | 90 | 1-butene | 85.2 |
| Comp. Ex. 1 | K2441 | 0.008 (Water was not added.) | 80 | 1-butene | 77.5 |
| Comp. Ex. 2 | AMBERLYST 15 | 2.5 | 90 | trans-2-butene | 37.3 |
| Comp. Ex. 3 | DOWEX 88 | 5.0 | 90 | 1-butene | 10.4 |

TABLE 2

| | Selectivity (%) | Conversion ratio (%) |
|---|---|---|
| Example 1 | 99.2 | 95.9 |
| Example 2 | 99.1 | 94.9 |
| Example 3 | 98.8 | 92.9 |
| Example 4 | 99.1 | 96.7 |
| Example 5 | 98.9 | 91.2 |
| Example 6 | 98.2 | 86.8 |
| Comp. Ex. 1 | 97.2 | 79.7 |
| Comp. Ex. 2 | 95.1 | 39.2 |
| Comp. Ex. 3 | 91.5 | 11.4 |

EXAMPLE 7 AND COMPARATIVE EXAMPLE 4

To examine the effects of the addition of water in inhibiting the catalyst deterioration, productions of sec-butyl acrylate were carried out by a fixed-bed continuous process under the conditions as listed in Table 3, with the water contents in the reaction systems adjusted to 0.12 wt % (Example 7) or 0.009 wt % (Comparative Example 4). In each reaction system, hydroquinone monomethyl ether was added as a polymerization inhibitor in a concentration of 200 wt ppm based on the weight of acrylic acid. The reactions were carried out at different contact times (SV) of acrylic acid with the catalysts, so that the reactions started at the same initial reaction rate. During the reactions, specific activities of the catalysts were calculated by the following equation.

Specific activity=[reaction rate during the continuous reaction process]/[initial reaction rate]

The acrylic acid throughput per unit volume of catalyst by which the catalytic activity was reduced to one-half is listed in Table 3.

The data as shown in Table 3 show that the catalyst deterioration was inhibited when the reaction system contained water in the concentration according to the present invention.

TABLE 3

| | Example 7 | Comparative example 4 |
|---|---|---|
| Catalyst | AMBERLYST 16 | AMBERLYST 16 |
| Water content (wt %) | 0.12 | 0.009 |
| Reaction temperature (° C.) | 75 | 75 |
| Butene | MTBE-BBS | MTBE-BBS |
| Molar ratio of butene/acrylic acid | 4 | 4 |
| Reaction pressure (kg/cm²G) | 15 | 15 |
| SV (hr$^{-1}$) | 0.5 | 2.5 |
| Half-life of catalyst (cc-AA/cc-Cat)* | 250 | 100 |

MTBE-BBS: A mixture which comprises 35 wt % of n-butenes and 65 wt % of butane and is obtained by feeding the $C_4$ distillates resulting from catalytic cracking of petroleum into a MTBE apparatus and then removing iso-butene therefrom.
*: acrylic acid throughput per unit volume of catalyst by which the catalytic activity was reduced to one-half

INDUSTRIAL APPLICABILITY

According to the present invention, sec-butyl acrylate, which is useful as the materials for pressure sensitive adhesives, adhesives, paints or the like, can be prepared in a high conversion ratio, such as 85 to 98%, with a high selectivity, such as 98.0 to 99.5%, while inhibiting catalyst deterioration.

What is claimed is:

1. A process for producing sec-butyl acrylate comprising allowing acrylic acid to react with a butene selected the group consisting of butene-1, trans-2-butene cis-2-butene, in a molar ratio of butene/acrylic acid ranging from 1 to 6, in the presence of an ion exchange resin having sulfo groups, in a liquid-phase reaction system containing 0.01 to 1.50 wt % of water, at a reaction temperature of 40 to 120° C.

2. The process of claim 1, wherein the reaction of acrylic acid and the butene is carried out by a batch process in the presence of 2 to 20 wt % of the ion exchange resin, based on acrylic acid, at a reaction pressure of 3.0 to 40 kg/cm²G.

3. The process according to claim 2, including the step of adding water to form the liquid-phase reaction system to contain 0.01 to 1.50 wt % of water.

4. The process of claim 1, wherein the reaction of acrylic acid and the butene is carried out by a fixed-bed continuous process at a contact time of the acrylic acid with the ion exchange resin [acrylic acid volumetric flow rate (cc/hr)]/[amount of packed dry ion exchange resin (cc)] of 0.01 to 10 hr$^{-1}$, at a reaction pressure of 3.0 to 40 kg/cm²G.

5. The process of claim 1, wherein the reaction of acrylic acid and the butene is carried out in the presence of 10 to 2,000 wt ppm of a polymerization inhibitor for acrylic acid and acrylic esters, based on the weight of acrylic acid.

6. The process of claim 5, wherein the polymerization inhibitor is selected from the group consisting of hydroquinone, phenothiazine, oxygen and hydroquinone.

7. The process of claim 1, wherein the molar ratio of butene/acrylic acid ranges from 2 to 5.

8. The process of claim 1, wherein the molar ratio of butene/acrylic acid ranges from 3 to 4.

9. The process of claim 1, wherein the molar ratio of butene/acrylic acid ranges from 3 to 6.

10. The process of claim 1, wherein the liquid-phase reaction system contains 0.01 to 1.0 wt % of water.

11. The process of claim 1, wherein the liquid-phase reaction system contains 0.01 to 0.50 wt % of water.

12. The process of claim 1, wherein the liquid-phase reaction system contains 0.02 to 1.50 wt % of water.

13. The process of claim 1, wherein the liquid-phase reaction system contains 0.02 to 0.50 wt % of water.

14. The process of claim 1, wherein the liquid-phase reaction system contains 0.02 to 1.2 wt % of water.

15. The process according to claim 1, including the step of adjusting the amount of water such that the liquid-phase reaction system contains 0.01 to 1.50 wt % of water.

* * * * *